United States Patent [19]

De Marco

[11] Patent Number: 4,618,490

[45] Date of Patent: Oct. 21, 1986

[54] METHOD OF TREATMENT OF ANIMAL AND HUMAN TISSUES DAMAGED BY BURNS AND FRANK VISIBLE GANGRENE

[76] Inventor: Peter T. De Marco, 7th Ave. and Erial Rd., Pine Hill, N.J. 08021

[21] Appl. No.: 726,062

[22] Filed: Apr. 23, 1985

Related U.S. Application Data

[63] Continuation of Ser. No. 156,915, Jun. 6, 1980, abandoned, which is a continuation of Ser. No. 919,087, Jun. 26, 1978, abandoned, which is a continuation of Ser. No. 87,621, Nov. 6, 1970, abandoned.

[51] Int. Cl.$^4$ .............................................. A61K 31/79
[52] U.S. Cl. ............................... 424/80; 424/DIG. 13
[58] Field of Search .......................... 424/80, DIG. 13

[56] References Cited

U.S. PATENT DOCUMENTS 3,337,406  8/1967  De Marco et al. .................... 424/80

*Primary Examiner*—Frederick E. Waddell
*Attorney, Agent, or Firm*—Steele, Gould & Fried

[57] ABSTRACT

The regeneration of animal tissues by intramuscular injections containing a substituted ethylamine in combination with a macromolecular substance for the purpose of intravascular transportation and or inhibition of hydrolysis of the compound after injection. The ethylamine moiety is selected from the group consisting of lidocaine, butethamine, chloroprocaine, dibucaine, hexylcaine, mepivacaine, piperocaine, benoxinate, naepaine, phenocaine, cyclomethycaine, proparacaine, pramoxine, tetracaine, dimethisoquin, procaine and 2-(4 imidazolyethylamine) or histamine and diphenhydramine. The macromolecule is selected from the group consisting of polyvinylpyrollidone, methyl cellulose, dextran, gelatin and polyoxyethylene sorbitan monooleate.

2 Claims, No Drawings

METHOD OF TREATMENT OF ANIMAL AND HUMAN TISSUES DAMAGED BY BURNS AND FRANK VISIBLE GANGRENE

This is a continuation of Ser. No. 156,915 filed June 6, 1980, now abandoned, which was a continuation of Ser. No. 05,919,087 filed June 26, 1978, now abandoned, which was a continuation of Ser. No. 05,087,621, filed Nov. 6, 1970, also abandoned.

This invention relates in general to the use of substituted ethylamines in the regeneration of animal tissues.

More specifically, this invention relates to composition adapted for intramuscular injections in living tissues of humans and animals in the treatment of damaged and destroyed tissues. The basic pathology in many diseases and traumatic states is the destruction of all cellular components in a given area. It is a localized phenomenom that usually and eventually affects other areas. Treatment is directed not only to the reversal of this pathology, via substituted ethylamines, in combination with a macromolecular substance, but also to the regeneration of the damaged and destroyed tissues to normal. Lysis of the necrotic material via an intravascular and exudative mechanism may also be observed. There is also observed the phenomenom that tissues surrounding a lesion which appeared to be normal will on occasion be broken down and the lesion will enlarge to where normal or genetically proper tissues are present before any healing occurs. The regeneration of animal tissues includes all cellular components present before their destruction, e.g. if a toenail and its bed is destroyed, regeneration of the toenail and its bed will occur to a state of anatomic normalcy. If a lesion destroys a print pattern, the print pattern will return to normal.

Throughout this specification, the term "cellular components" has been employed rather than the term "tissues". Although tissues are the final result which one can see and photograph, the fact remains that they are sequentially built from a multitude of cells, with the synthesis of protein playing an equally important role. Further, the term "cellular components" as employed herein means not only each individual cell, but also the proper fixation of each cell to other cells to form the final product which may be blood vessels, bones, cartilage, nerves, dermis and epidermis, and the harmonious union of these components to form identifiable tissues.

"Regeneration" as used herein means the replacement of dead or absent cells by cells that are morphologically the same, by the re-establishment of cellular components.

The nucleic acids play a vital role in the synthesis of proteins from amino acids and this is a major part of, among other things, growth and differentiation of the cellular components as above defined. The cellular components under consideration are those which may have been destroyed primarily by trauma, by the release of localized toxins or by other antagonistic substituted ethylamines. The net result is the impairment of the mechanism responsible for the proper and specific growth, re-growth and repair of the cellular components. This mechanism has to do with, among other things, the synthesis of proteins by nucleic acids.

It is proposed that the intramuscular injection of animal tissues with a specific substituted ethylamine combined with the use of a macromolecule for intravascular transportation purposes and/or to inhibit hydrolysis of the substituted ethylamine results in activating, speeding up and causing the mechanism responsible for the regeneration of cellular components to come into play and to cause controlled cellular growth via a specific sequential predetermined plan of regeneration and re-growth. It is further postulated that this mechanism involves the synthesis of proteins by the nucleic acids. This process is totally different from that of physiologic regeneration.

When considering procaine, it may be classified as an anaesthetic and its chemical structure can be set forth as follows:

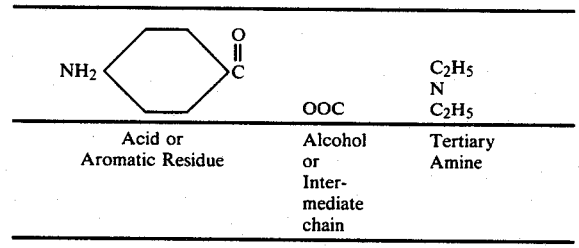

| Acid or Aromatic Residue | Alcohol or Intermediate chain | Tertiary Amine |

In this particular application procaine is considered as a substituted ethylamine as follows:

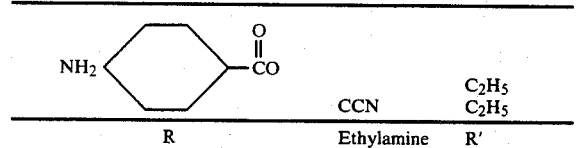

| R | Ethylamine | R' |

This interpretation allows it to be contrasted to other substituted ethylamines to which it is related and antagonistic as follows:

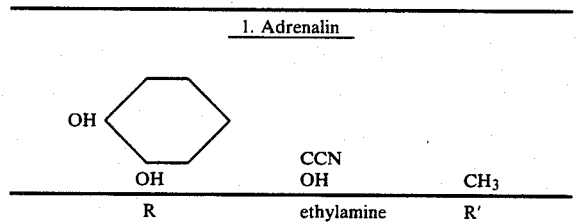

| R | ethylamine | R' |

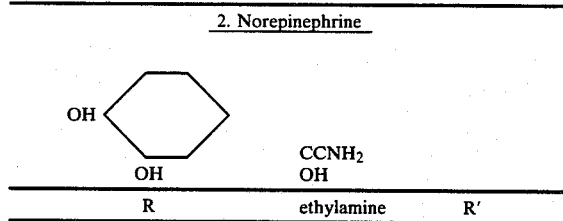

| R | ethylamine | R' |

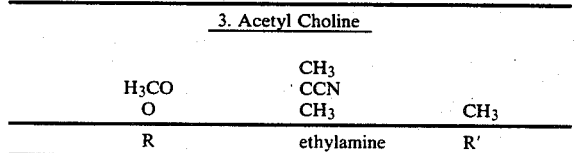

| R | ethylamine | R' |

It is postulated that acetyl choline release is the first step in the liberation of norepinephrine. It is theoretically possible that a specific antagonistic substituted ethylamine molecule blocks or inhibits this release.

In contrast to aliphatic and cyclic substitution of the ethylamine moiety, heterocyclic substitution brings us to the following compound which may be either antagonistic, if found in a free or unbound state, or related if it occurs in bound form.

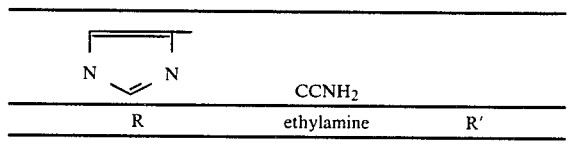

| R | ethylamine | R' |

The release of catecholamines superimposed upon the effect of released free histamine plus other toxins is probably the reason for the chemical destruction of the cellular components and also for the destruction of the mechanism responsible for the repair or replacement of the cellular components by more primitive cells.

One of the great, if not the greatest, difficulty in the interpretation of the effects and physiologic role of histamine is the problem of its ubiquitousness and its binding capacity with micro and macromolecular substances which occur naturally. Injection of labeled $C^{14}$ free histamine into the body and following its metabolism in no way insures that the histamine will become an integral part of the true physiologic histamine system. Perhaps it lacks the proper transportation or binding system to fit into the body's true metabolism. This fact represents another difficulty in the elucidation of its physiology.

Recently, G. Kahlson et al implicated histamine as relevant to wound repair and cellular multiplication in a paper entitled, "The Histamine Forming Capacity of Multiplying Cells", Journal of Physiology, London, Vol. 196, May 13, 1963, Pages 487–498. In a paper entitled, "Induced Synthesis of Histamine Microcirculatory Regulation and the Mechanism of Action of the Adrenal Gluco-Corticoid Hormones" published in Progr. Allergy, 1963, Vol. 7, Pages 187–212, Richard W. Schayer implicated histamine as relevant to the micro capillary circulation. For further background information, see also the article entitled, "The Effect of Cutaneous Burns on Histamine in Mice" by J. Dekanski, Vol 104 Journal of Physiology, London, 1955, Pages 151–160.

The results of the evidence presented in this specification would tend to indicate that certain substituted ethylamines have the function of regeneration of the cellular components and that it is possible that these substituted ethylamines activate the mechanism whereby the use of histamine bound, temperary binding, loose binding, or other binding is a step in the conversion of histamine to nucleic acids and that it is the incorporation of histamine into the nucleic acids which in turn causes the synthesis of proteins.

It is also known that the body metabolizes injected histamine several ways. One of these ways is the conjugation of histamine with ribose. Nucleic acids are composed of ribose, phosphoric acid, purine and pyrimidine bases. Additionally, there is a great deal of information with respect to histamine that apparently does not fit the current concepts of its physiologic role. Indeed, no definitive physiologic role has as yet been assigned to histamine in the body.

Among the examples of its multi-spectrum activities with no apparent relevance are the following facts:

(a) The presence of large amounts of histamine in juvenile diabetics, so large in fact, that the excess amount of histamine causes these patients to manifest with allergic symptoms. This is probably an attempt by the body to restore proper cellular growth and repair by a tremendous outpouring of histamine (bound and unbound). Improper cellular growth and repair is very striking in severe juvenile diabetics.

(b) Another good example is the large amount of histamine activity present in placental tissues. Theoretically its function should be the regulation of cellular growth via the nucleic acid mechanism. In spontaneous abortion, placental histamine activity is greatly diminished. Therefore, the use of a substituted ethylamine would theoretically prevent spontaneous abortion. Examples are presented below which tend to substantiate the above theories. This includes both human and animal. My solutions are comprised of the following compositions stated as contained in each cubic centimeter:

| Empiric Composition of Solution "A" | |
|---|---|
| Procaine Hydrochloride | 5 percent |
| Sodium Bisulfite | 0.2 percent |
| Benzyl Alcohol | 1.5 percent |
| Polyvinylpyrrolidone | 10 percent |
| Water q.s. | |
| Empiric Compound of Solution "B" | |
| Histamine Phosphate | .5 percent |
| Glycerine | .16 percent |
| Phenol | 2 percent |
| Polyvinylpyrrolidone | 10 percent |
| Water q.s. | |

The Ph is adjusted so that the solutions are compatible with intramuscular injection into living tissues.

The molecular weight of polyvinylpyrrolidone may range from 5,000 to 50,000 for both solutions.

The concentrations of procaine base or histamine base and polyvinylpyrrolidone must be adequate to insure a therapeutic concentration of the ethylamines and to effectively transport and/or prevent hydrolysis.

In order to heal the diseased part of tissues, initial saturation is required so that a solution in the range of from one to thirty c.c.'s per day is injected intramuscularly for a period of five days to three weeks. After saturation, the injections continue ranging from one to fifty c.c.'s once to three times per week. After the diseased part has evidenced the healing process, injections continue from once a week to twice a week with a dosage in the range of from one to fifty c.c.'s.

Then injections are continued as maintenance therapy. The dosages are titrated to the pathology being treated.

Such individual injections may contain from about 50 mgms. to about 2.5 grams of procaine hydrochloride and from about 100 mgms. to about 5 grams polyvinylpyrrolidone having molecular weight in the range of 5,000 to 50,000.

In like manner, the injection may contain histamine phosphate from about 0.55 mgms. to about 27.5 mgms. and about 10 mgms. polyvinylpyrrolidone to about 0.5 grams.

The following are illustrative case histories showing treatment according to the present invention:

1. The subject was a white female, age thirty, with a past history of three spontaneous abortions at ages twenty-six (three months), twenty-eight, (three months) and twenty-nine (four months). At age thirty, weekly intramuscular injections commenced for four months prior to conception and continued throughout the pregnancy. The pregnancy proved uneventful with no restrictions or special conditions other than the weekly injections. The result was a normal term pregnancy and normal birth.

As was noted earlier, the histamine activity of placental tissues in humans as evidenced by a low level of plasma histaminase is indicative of spontaneous abortion. Diamine oxidase oxidizes the ethylamine in accordance with the following formula:

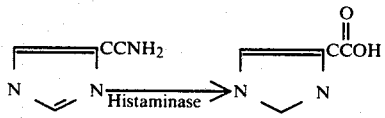

The effect of this is to render the histamine inactive. The probable role of histaminase in pregnancy is to destroy any unbound or free histamine because the unbound histamine is an antagonist to proper cellular growth.

2. In this case, a twenty-seven year old white male with third degree burns of the right leg covering about forty percent of the leg on the anterior and lateral surfaces resulting from an ignited spill of gasoline was treated. Intramuscular injections were started and consisted of five c.c. daily Monday through Friday. Injections continued for a period of three months at which time the leg completely healed.

The basic pathology of third degree thermal burns is the destruction of arteriol and cellular patterns. If the mechanism for the regeneration of cellular components is not activated, there is no regeneration of the epidermis, dermis, etc., because the dermis and the deeper tissues have been destroyed. The dermis (corium) is irreversibly injured and extensive scar formation normally occurs because of the fibro-blastic proliferation. Concomitantly, there are released great quantities of toxins, catecholamines and free histamine. By activating the regenerative mechanism, no scar formation results and epithelialization proceeds normally as does all of the replacements of the burned area, so that the leg returns to anatomic normalcy.

3. In the case of a fifty-three year old white male with a leg ulcer, three to four inches in diameter on the medial malleolus, the ulceration was due to the destruction of the cellular components in the area. Before the acute necrosis occurred, there was present a rather extensive scar which was not visible when starting the intramuscular substituted ethylamine therapy because the scar had also become necrotized.

Following daily injections of 10 c.c. over a period of two weeks and then two injections per week for seven months, the leg ulcer completely healed. When the leg healed, the scar came back to its original position and dimensions while the remainder of the area healed with normal tissues.

4. The case involves a sixty-three year old white female with frank visible gangrene in two places on the foot. Examination indicated that previous to the gangrene, the two areas had scarified. Following intramuscular injections daily of 10 c.c. for a period of two weeks and then three injections per week for a period of one year, the foot healed and the small areas of original scar tissue were replaced with scar tissue. The print pattern on the rest of the foot and all her other cellular components returned to normal.

Cases Number 3 and 4 are taken as one because of the great similarity in the results and original pathology. The two main points to be made are that (a) whatever tissues were present before the acute state of necrosis, they are replaced as previously. Apparently once the coding information has been "set" via a localized inflammatory reaction and scar tissue has been formed via fibroblastic proliferation, the scar tissue is replaced while the surrounding tissues heal normally. (b) That the destroyed cellular components are sequentially assembled to a state of normalcy.

5. The next case involves a fifty-three year old white male having wet gangrene of the second toe with the nail bed also necrotic. In accordance with prior practice, amputation would have been the only course of therapy. In accordance with the present invention, daily intramuscular treatment of 10 c.c. for a period of two weeks immediately isolated the condition and began to reverse the pathology. Injections continued at the rate of two per week for seven months. Regeneration of the toe, including the nail and its bed, nerves, print patterns, etc., resulted. In short, treatment resulted in an anatomically and physiologically normal toe.

It may be observed that fibrinolysis of the necrotic material occurs in a definitive line of demarcation as the regeneration takes place from the "good" sides. That material not lysed is mechanically pushed off by the regeneration of the tissues underneath the area of the isolated necrosis. It may also be observed that regeneration of the nail and its bed takes place sequentially with the remainder of the toe, so that complete healing of the toe and regrowth of the nail occur simultaneously. It is further observed that the phenomenon of controlled cellular growth (as distinguished from uncontrolled cellular growth) originates from areas of non-necrotic tissues. By so doing, growth occurs from all sides until the area is regenerated. It is apparent that regeneration and healing do not occur haphazardly, but in a definitive sequential pattern.

The previous specific examples of the invention relate to either the administration of procaine hydrochloride-polyvinylpyrrolidone solution or histamine phosphate-polyvinylpyrrolidone solution. However, in place of procaine hydrochloride, there also may be used other non-antagonistic substituted ethylamines. Also, in place of polyvinylpyrrolidone there may be used other macromolecular polymeric agents such as methyl cellulose, dextran, gelatin, polysorb, and derivatives thereof.

There may be used other non-antagonistic substituted ethylamines and they may be associated with a suitable polymeric agent for intravascular transportation and/or inhibition of hydrolysis when injected into living tissues as follows: butacaine, tetracaine, dibucaine, piperocaine, hexylcaine, phenocaine, lidocaine, ethylaminobenzoate, butylaminobenzoate, heptacaine, nupercaine, chloroprocaine, procaine borate, 2-diphenyl methoxy-N.N-dimethylamine or diphenhydramine.

In case number 6, a diabetic white male, age fifty-eight was observed with a necrotic, gangenous area measuring about 5.5 cms. in diameter and approximately 5 to 7 mms. in depth on the sole of the foot. The area of gangrene was confined to an area of approximately 3×2 cms. Daily intramuscular injections of 10 c.c. for a period of two weeks and then twice a week for seven months caused healing of the entire area with the redevelopment of the print pattern to a state of normalcy and matching the print pattern precisely with the old print pattern.

In treating chickens, five years old or older that have naturally lost their feathers and quills on the dorsum of the back in a relatively large area measuring approximately 15 cms. by 10 cms., intramuscular injections of from 2 c.c. to 4 c.c. were administered daily for a period of two weeks. Intramuscular injection therapy then continued at a rate of three times per week for a period of eight weeks. This resulted in the reappearance of the quills from beneath the surface of the skin. Feathers will grow from these quills so that the entire area will exhibit a regeneration and regrowth of the lost quills and feathers.

I claim:

1. A method of minimizing scarring in a patient suffering from burns which comprises administering to said patient by injection into tissues adjacent said burn injury an aqueous composition of about 50 mg. to about 2.5 g. of a pharmaceutically acceptable salt of procaine and about 100 mg. to about 5 g. of polyvinylpyrrolidone having a molecular weight of 5,000 to 50,000.

2. The method of claim 1 wherein said aqueous composition comprises about 1.5 percent of an alcohol, about 5 percent of a procaine salt and about 10 percent of polyvinylpyrrolidone.

* * * * *